United States Patent
Baur

(10) Patent No.: US 8,100,891 B2
(45) Date of Patent: Jan. 24, 2012

(54) MEDICAL APPLIANCE WITH MAGNETIC ADJUSTMENT APPARATUS

(75) Inventor: Stephan Baur, Tübingen (DE)

(73) Assignee: ERBE Elektromedizin GmbH, Tüingen (DE)

( * ) Notice: Subject to any disclaimer, the term of this patent is extended or adjusted under 35 U.S.C. 154(b) by 1051 days.

(21) Appl. No.: 11/988,220

(22) PCT Filed: Jun. 27, 2006

(86) PCT No.: PCT/EP2006/006203
§ 371 (c)(1),
(2), (4) Date: Jan. 3, 2008

(87) PCT Pub. No.: WO2007/006419
PCT Pub. Date: Jan. 18, 2007

(65) Prior Publication Data
US 2009/0125024 A1  May 14, 2009

(30) Foreign Application Priority Data
Jul. 8, 2005  (DE) .......................... 10 2005 032 032

(51) Int. Cl.
*A61B 17/00* (2006.01)
(52) U.S. Cl. ................... 606/1; 81/52; 606/34; 173/213
(58) Field of Classification Search ........................ None
See application file for complete search history.

(56) References Cited

U.S. PATENT DOCUMENTS

| 3,461,874 A | 8/1969 | Martinez |
| 5,586,823 A * | 12/1996 | Carr ............................... 366/274 |
| 6,171,265 B1 | 1/2001 | Novak et al. |
| 6,198,175 B1 * | 3/2001 | Kalb et al. ................... 307/10.1 |
| 6,537,210 B1 | 3/2003 | Wulfsberg et al. |
| 6,616,602 B1 | 9/2003 | Witte et al. |
| 2004/0230214 A1 | 11/2004 | Donofrio et al. |
| 2004/0236183 A1* | 11/2004 | Durell ........................... 600/173 |
| 2010/0217354 A1* | 8/2010 | Weiss et al. ..................... 607/61 |

FOREIGN PATENT DOCUMENTS

| DE | 295 19 706 U1 | 12/1995 |
| DE | 197 18 189 A1 | 4/1997 |

(Continued)

OTHER PUBLICATIONS

General Reed Switch Theory.*

*Primary Examiner* — Sam Yao
*Assistant Examiner* — Lynsey Crandall
(74) *Attorney, Agent, or Firm* — Dickstein Shapiro LLP

(57) ABSTRACT

A medical appliance with an adjustment apparatus, such that cleaning of the medical appliance, constructed with the adjustment apparatus, can be carried out reliably and simply. The medical appliance includes a first setting device disposed at an outer side on a housing of the appliance, and a second setting device disposed in the interior of the appliance. The second setting device is designed to actuate a setting element for adjustment of a controllable and/or regulatable device. The first setting device and the second setting device each comprise magnet elements, by which the first setting device cooperates with the second setting device in such a way that the one setting device actuates the other setting device for the transmission of adjustments, the cooperation of the setting devices being achieved by way of a magnetic coupling.

16 Claims, 2 Drawing Sheets

FOREIGN PATENT DOCUMENTS

| | | |
|---|---|---|
| DE | 299 17 914 U1 | 10/1999 |
| DE | 100 63 693 C1 | 8/2002 |
| DE | 697 19 689 T2 | 5/2003 |
| DE | 20 2004 002 409 U1 | 5/2004 |
| DE | 696 32 061 T2 | 10/2004 |
| EP | 1 320 319 B1 | 12/2003 |
| EP | 0 858 293 B1 | 3/2004 |
| GB | 1 381 387 A | 5/1973 |
| JP | 59-150142 U | 10/1984 |

\* cited by examiner

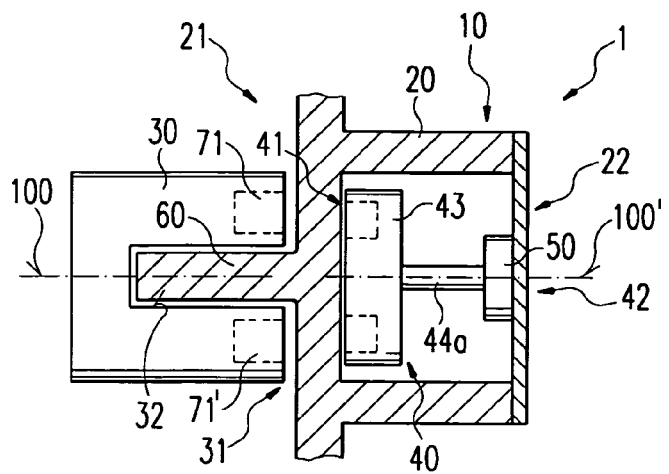
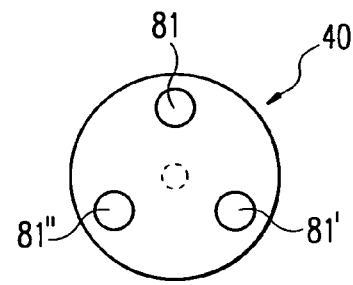
Fig. 1a
Fig. 1b
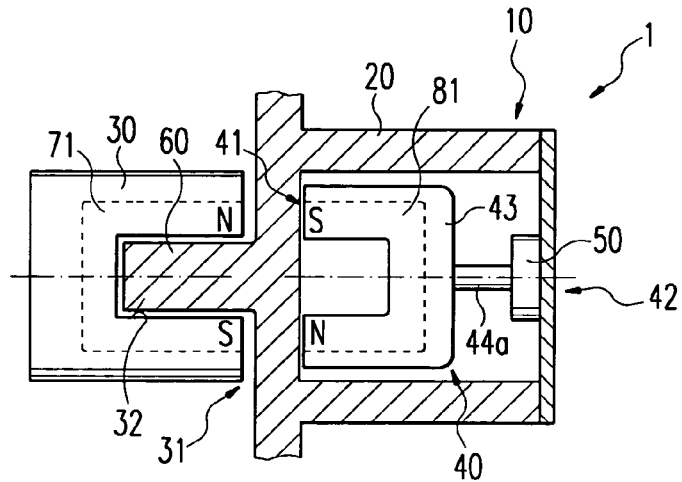
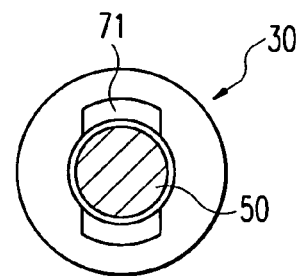
Fig. 2a
Fig. 2b
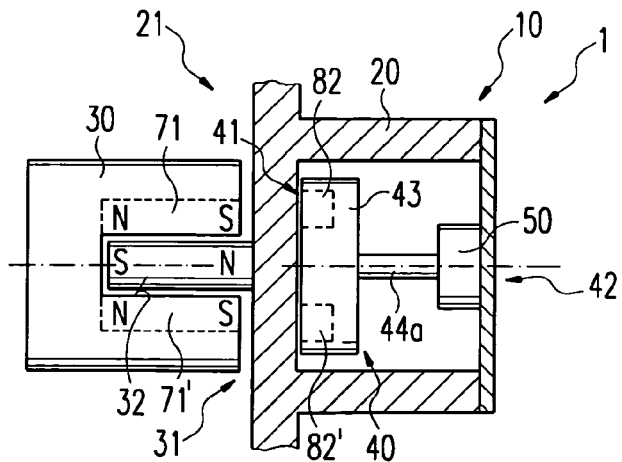
Fig. 3

MEDICAL APPLIANCE WITH MAGNETIC ADJUSTMENT APPARATUS

FIELD OF THE INVENTION

Disclosed embodiments of the invention relate to a medical appliance, and in particular to a medical appliance with a magnetic adjustment apparatus.

BACKGROUND OF THE INVENTION

Due to the purposes for which they are employed, medical appliances such as those for high frequency (HF) surgery, are subject to high demands regarding their reliability during use and regarding possible methods of cleaning and in particular disinfecting them. Appliances with an adjustment apparatus, for example to change settings so that they can operate in various modes or to make other desired adjustments, can often not be adequately cleaned because of the way the control elements (such as, e.g., knobs, sliders or similar input devices) are constructed. On one hand, the input devices themselves may incorporate inaccessible places, and on the other hand because of the way they are positioned on the medical appliance they interfere with access to other parts of the appliance that need cleaning. Furthermore, the various kinds of adjustment apparatuses used in known medical appliances are constructed such that contaminants from the surroundings are able to penetrate the interior of the appliance. This can occur, for example, when the input device accessible from the exterior is connected by a shaft or similar connecting element to a controllable and/or regulatable device in the interior of the appliance. Insufficiently cleaned appliances present a source of danger to the patients' health. In addition, the functionality of the appliance can be impaired by contaminants.

To avoid the intrusion of contaminants, conventional appliances often include sealed connecting elements, which are intended to prevent liquids or other germ-containing substances from entering. However, a completely tight seal cannot be provided in this way.

The document EP 0 858 293 B1 discloses a magnetic switching element for actuating a surgical device. A handpiece for motor-driven surgical systems is provided in which switches are fixed to the outside of a housing and physically isolated from the "interior" of the handpiece. This isolation ensures that the switches provide no leakage path such as described above, to electronics situated within the handpiece. The surgical device is activated and/or inactivated by way of the switches, which in this case cooperate with a Hall-effect sensor disposed in the interior of the handpiece. In this process, a permanent magnet disposed in each of the switches generates a magnetic field that, when the switches are actuated, is coupled to the sensor and/or decoupled from it and thus brings about operation of the surgical system.

In this system the penetration of contaminants into the interior of the device, in this case the handpiece, is indeed prevented, but an elaborate construction is required for the interaction between switch and sensor. Furthermore, the problem of inadequate cleanability of the switches and their surroundings still remains.

The objective of the disclosed embodiments is thus to develop a medical appliance in such a way that cleaning of a medical appliance equipped with an adjustment apparatus can be done in the simplest possible way, while simultaneously keeping the structure and manner of function of the device likewise as simple as possible.

BRIEF DESCRIPTION OF THE DRAWINGS

The invention is described with reference to exemplary embodiments, which are explained in greater detail with reference to the drawings.

FIG. 1a illustrates part of a medical appliance with an adjustment apparatus in a first preferred embodiment, drawn schematically in side view.

FIG. 1b illustrates a second setting device of the adjustment apparatus according to the first preferred embodiment, drawn schematically in front view.

FIG. 2a illustrates part of a medical appliance with an adjustment apparatus in a second preferred embodiment, drawn schematically in side view.

FIG. 2b illustrates a first setting device of the adjustment apparatus according to the second preferred embodiment, drawn schematically in front view.

FIG. 3 illustrates part of a medical appliance with an adjustment apparatus in a third preferred embodiment, drawn schematically in side view.

DETAILED DESCRIPTION OF THE INVENTION

Figure 4:
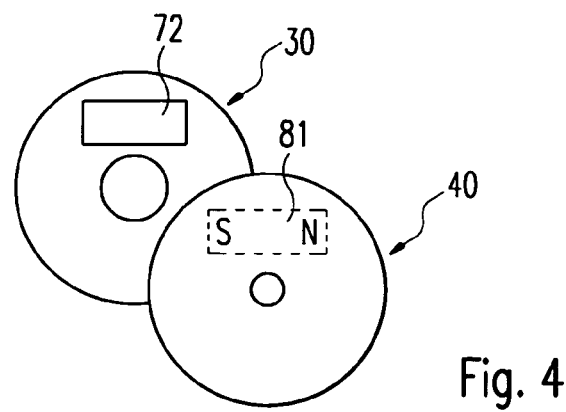
FIG. 4 is a simplified representation of a perspective view of a first and a second setting device in a fourth preferred embodiment.

Disclosed embodiments of the invention include a medical appliance with an adjustment apparatus that includes a first setting device, disposed on an external surface of the appliance's housing, as well as a second setting device that is disposed in the interior of the appliance and is designed to actuate a setting element for adjusting the setting of a controllable and/or regulatable device. The first setting device and the second setting device include magnet elements, by which the first setting device cooperates with the second setting device in such a way that the one setting device actuates the other setting device so that intended adjustments are transmitted, the cooperation of the setting devices being brought about by a magnetic coupling.

An adjustment undertaken from the outside by means of the first setting device can be transmitted to the interior of the medical appliance by way of the magnetic coupling without a need for an opening in the housing. For example, the first setting device is actuated by a user, and the movement thus made by the first setting device is transmitted by way of the magnetic coupling to the second setting device, so that the latter in turn can move the setting element. Then, by means of the setting element, the controllable and/or regulatable device in the interior of the medical appliance can be adjusted. The fact that the second setting device, disposed in the interior, is actuated by a magnetic coupling simultaneously enables the appliance to function in a simple manner, employing a mechanism that is itself simple and economical to manufacture. Because the first setting device is attached to the device by way of the magnetic coupling, it can be removed for cleaning purposes without any problems. This enables a comprehensive, easily performable disinfection of the device.

In a first preferred embodiment, the magnet elements are constructed as permanent-magnet elements or as ferromagnetic elements, such that at least one of the setting devices includes at least one permanent-magnet element. To form the magnetic coupling through a wall of the housing, the magnetic elements are situated at both the first and the second setting devices, which represents an especially simple and economical design of the apparatus. Depending on the application and on the forces to be transferred through the adjustment apparatus, the magnetic coupling can be achieved by the interaction of permanent-magnet elements either with one another or with ferromagnetic elements. To obtain a strong magnetic coupling, the first setting device and the second setting device are situated opposite one another, separated by the housing. The housing is preferably constructed without any openings in a region where the setting devices are operating, because the transmission of the desired adjustment occurs exclusively by way of the magnetic coupling of the setting devices.

One solution in accordance with preferred embodiments of the invention provides that the one setting device is actuated in such a way that the one setting device entrains the other setting device. To put it another way, actuation of the one setting device is brought about by the other setting device in such a way that one of the setting devices entrains the other. The movement of the one setting device is transferred to the other setting device and the entrained setting device follows the movement of the entraining setting device.

The first setting device in one preferred embodiment is constructed such that it can be placed on a receiving element that is preferably made integral with the housing. If the receiving element is integral with the housing, it can be manufactured in a simple way and can be cleaned with no problems because there are no joints, niches or similar poorly accessible sites. The receiving element can, for example, be welded to the housing or can be produced directly with the housing using a casting process. The receiving element is formed to be integral with the housing and is immovably attached thereto. The receiving element is thus suitable for receiving setting devices that transfer the desired adjustments by a rotational movement. In other words, the setting device is rotatably disposed on the receiving element.

It would also be possible to control the controllable and/or regulatable device in the interior of the appliance, e.g. by way of a controlling device, so that an adjustment produced there would be transferred from the interior of the appliance outward, to the first setting device. The purpose of this arrangement could be, for example, to make changes to the settings visible from the outside, by way of the first setting device.

If the transmission of an intended adjustment is to be carried out by means of rotational movements of the first setting device, the magnet elements of the first setting device and the second setting device should be disposed with respect to one another so that they form a magnetic field that is not rotationally symmetric about an axis of rotation of the setting devices. When the first setting device is turned, therefore, the magnetic field undergoes an alteration such that the magnetic flux between the magnet elements is weakened. In order to return the magnetic flux to its maximal value, the second setting device follows the first setting device, so that the desired actuation of the setting element can be undertaken. If the magnetic field that is responsible for the magnetic coupling were to form so as to be symmetric about the setting devices' axis of rotation, the magnetic flux would remain unchanged even when the first setting device is rotated and the coupled setting device would not follow the one that is rotating, and it would be impossible to actuate the setting element.

In addition to transmission of the desired adjustments by means of turning knob and moment of torque, transmission can also be implemented by way of a sliding controller or similar shiftable element. The actuation of the setting element would be brought about by a linear movement of the setting devices. Preferably the first setting device is designed to be disposed in a guide means on the housing within which it is held and can be shifted substantially linearly relative to the housing. In the embodiment involving a sliding controller, reliable entrainment of one setting device by the other can be guaranteed. The necessary alteration of the magnetic flux described above is achieved here by simple means.

Advantageously, the first setting device is constructed as a knob element for actuation by the user of the medical appliance. Knob elements are economical and can be manufactured in an ergonomically advantageous way according to the user's desires. Furthermore, knob elements can be easily disposed on the corresponding receiving element.

The second setting device preferably includes a carrier element on which the magnet elements required for the magnetic coupling are disposed, for example at an end that faces towards the outside of the appliance. The setting element for adjusting the controllable and/or regulatable device is attached to the carrier element at an end directed into the interior of the appliance. The controllable and/or regulatable device in this case can be designed as a potentiometer, a valve or similar device. If the controllable and/or regulatable device is provided as a potentiometer, for instance, the setting element is constructed as a shaft for transmitting a rotary movement or as a rod for transmission of a linear movement. That is, the setting element attached to the carrier element or the second setting device is then, e.g., provided as the setting element of the potentiometer and when actuated brings about a corresponding change in resistance. It is also possible, e.g., for a valve to be adjusted or its position altered by way of the rod or similar setting element. In order to achieve an adjustment of the controllable and/or regulatable device, its housing is fixed to or within the medical appliance in such a way as to enable interaction with the setting element; that is, the setting element is movable relative to the associated housing. The housing of a rotatable potentiometer, for example, is fixed so that it is situated opposite to the carrier element in the direction of the axis of rotation, at the end pointing towards the interior of the appliance. Hence the setting element is then actuated by way of the second setting device, whereas the second setting device in turn is caused to move by way of the first setting device. In this way, transmission of the adjustment to the setting element can thus be implemented substantially without any wear and tear.

Owing to the magnetic coupling of two setting devices such as are described above, a required adjustment of the medical appliance can be transmitted in the simplest way, and the desired operating mode can be reliably put into effect.

To form a magnetic coupling that is as effective as possible, i.e. an effective magnetic field that satisfies the requirements of the adjustment apparatus in accordance with the embodiments of the invention, the first setting device includes at least one magnet element disposed on an end face at an end of the setting device that is directed towards the interior of the appliance. The same applies to the second setting device, situated opposite the first setting device. The latter should also have the magnet element or elements disposed on an end face of the setting device, in this case at the end that is directed towards the outside of the appliance. This ensures a reliable magnetic coupling, because the magnet elements of the setting devices are situated substantially opposite one another.

Due to the short distance between the magnet elements of the setting devices, a strong magnetic field can develop.

In one preferred embodiment, at least one of the setting devices includes a horseshoe magnet. Magnets of this kind are economical to purchase and ensure that the one setting device will be entrained by the other, in particular during transmission of a rotary movement, in an especially simple and reliable way. Instead of horseshoe magnets, bar magnets can also be used.

If permanent magnets are provided at both setting devices, these enable a strong magnetic field to be formed. The permanent magnets can also be coupled to an iron element, e.g. a yoke, or another ferromagnetic material. This represents an especially favorable design of the adjustment apparatus. Furthermore, there is no need to pay attention to a particular arrangement of the ferromagnetic elements with regard to polarity. For example, the first setting device can be constructed with the horseshoe magnet while an iron yoke is provided at the second setting device. Permanent magnet and yoke produce the magnetic field required for the magnetic coupling.

When bar magnets are used at the setting devices, the oppositely situated bar magnets are accordingly disposed with oppositely oriented poles, to enable the formation of the magnetic fields. Here, again, the magnetic field can be formed by a combination of permanent magnet and, for instance, an iron element.

One embodiment of the invention provides for the first setting device to be constructed so that it is fixed to the appliance by a force generated owing to the magnetic coupling. That is, the magnetic coupling, i.e. a force of attraction, makes it possible for the setting device to be held securely to the appliance. In this case the setting device can be retained on the housing or the appliance exclusively by this magnetic coupling, but the receiving element of the first setting device can also supplement this retaining force. The magnetic coupling between the setting devices thus is in itself sufficient to keep the first setting device fixed to the appliance. In order to develop a supplementary (additional) retaining force by way of the receiving element, the receiving element is constructed as a permanent-magnet element or is made of a ferromagnetic element, or it at least includes such elements. These then act together with the magnet elements of the setting device, and in some cases with the magnet elements of the opposite setting device. In this way it is possible to enhance the magnetic coupling for entraining the one setting device by the other, and also the retaining force that holds at least the first setting device, and in some cases both of them, to the housing or appliance.

Depending on the particular application, therefore, it is sufficient for only the first setting device, i.e. the one on the outside of the housing, to be disposed on the housing by way of the receiving element. However it would be possible for the second setting device also to be seated in another receiving element.

If the receiving element includes a bar magnet, another bar magnet disposed in parallel within the first setting device but with oppositely oriented poles can increase the force that holds the setting device to the appliance, i.e. to the receiving element, while all bar magnets act to form a strong magnetic coupling to the opposite setting device and the correspondingly constructed magnet elements. The design of the receiving element as a ferromagnetic element likewise increases the retaining force for a setting device constructed with a permanent magnet.

If the setting devices include more than one permanent magnet, for instance several bar magnets, these can preferably be disposed on the end face of the setting device. The magnets are preferably spaced apart over the end faces by uniform distances in order to form a uniform magnetic field. Thus it is possible for two or three bar magnets to be arranged on the end face of the first setting device, in which case the second setting device includes additional bar magnets or ferromagnetic elements attached with the appropriate polarity. When the bar magnets are arranged on the corresponding end faces of the setting devices, the magnets can each be disposed with one of their ends at the end face; i.e., the one pole is directed towards the housing, whereas the other pole is directed away from the housing. It is also possible for the magnets to be attached to the end face of the associated setting device by means of a flat side of the bar magnet, which extends between the poles. This simplifies the attachment of the magnets to the setting devices.

The magnet elements that create the magnetic coupling can be placed on the setting devices, inserted into them or embedded in them in such a way that access from outside is no longer possible. The last of these embodiments provides especially effective protection of the magnets from mechanical stresses.

Preferably the first setting device and the receiving element are constructed so that when the setting device is placed on the receiving element, it comes into locking engagement therewith. This provides a means of secure retention of the setting device in addition to the magnetic forces. In the case of rotatable knob elements, care should be taken that rotary movement remains possible despite the locking engagement (e.g., guidance within a groove).

Furthermore, in one preferred embodiment it is additionally provided that the setting element consists of at least one reed contact for actuating and/or adjusting the controllable and/or regulatable device, in which case the first setting device is constructed such that when it is actuated, the reed contact can be actuated. For example, the controllable and/or regulatable device can be provided as a switch with a resistance that can be connected by way of the reed contact. It is advantageous for the second setting device to include several reed contacts, which can be actuated in sequence by the first setting device, for instance when the latter is linearly shifted along the housing of the medical appliance. Thus multiple resistances can be connected or disconnected, so that in this way an alterable resistance is implemented. The reed contacts allow an arbitrary number of components to be actuated in order to implement the desired adjustment.

In the following description, the same reference numerals are used for identical parts or parts with identical actions.

FIG. 1a illustrates part of a medical appliance 1 with an adjustment apparatus 10 in a first preferred embodiment, drawn schematically in side view. FIG. 1b is a schematic drawing in front view of a second setting device 40 of the adjustment apparatus 10 according to the first preferred embodiment. The adjustment apparatus 10 is constructed on the medical appliance 1. In order to achieve an adjustment (e.g. for a particular mode of operation), a desired setting (i.e., ultimately a signal) can be transmitted by way of a first setting device 30 into said housing in order to alter the setting, i.e. the signal, at a setting element 44. The first setting device is situated on an outside 21 of a housing 20 of the appliance 1. The second setting device 40, which receives the setting transmitted by the first setting device 30 and accordingly actuates the setting element 44, is situated in the interior 22 of the appliance 1. The setting element 44 is constructed so as to adjust or alter the setting of a controllable and/or regulatable device 50. In the final analysis, therefore, the second setting device comprising the setting element is moved by the first setting device, by way of the magnetic coupling.

The two setting devices 30, 40 must be coupled to one another so that the adjustment setting input can be transmitted from outside by way of the first setting device 30 to the second setting device 40. Although they are coupled together, it is provided that the two setting devices 30, 40 are physically isolated from one another, so that the appliance 1 can easily be cleaned and does not make available any route by which germs could enter the interior 22 of the appliance 1. In this case, the coupling is achieved by a magnetic field, in that the two setting devices are provided with magnet elements 71, 81 that connect the setting devices 30, 40 to one another (force of attraction) while causing the setting devices 30, 40, or in some cases only the first setting device 30, to be retained on the medical appliance 1.

In this exemplary embodiment, the first setting device 30 is intended to transmit a rotary movement, i.e. a moment of torque, to the second setting device 40. For this purpose, the housing 20 of the medical appliance 1 includes on its outside 21 a receiving element 60, constructed integrally therewith, which receives the first setting device 30. The first setting device 30 is here provided, for instance, as a turning knob with a centrally situated recess 32, so that the knob can be seated on the receiving element 60 by way of the recess 32. Recess 32 and receiving element 60 interact with one another in such a way that the turning knob can be rotated on the receiving element 60. The second setting device 40 is disposed in the housing 20 in such a way that the two setting devices 30, 40, while separated from one another by the housing 20, are situated opposite one another. In other words, the axes of rotation 100, 100' of the setting devices 30, 40 ate substantially aligned with one another.

The first setting device 30 here is designed with magnet elements 71 situated at an end face of the setting device 30, at an end 31 thereof that is directed towards the interior of the appliance, so that the magnets aim towards the medical appliance 1.

The second setting device 40 includes a carrier element 43 on which the magnet elements 81 ate disposed at an end 41 that faces the outside of the appliance. A shaft 44a is attached at an end 42 directed towards the interior of the appliance to serve as a setting element to adjust the controllable and/or regulatable device 50. The shaft 44a of the potentiometer (i.e. the controllable and/or regulatable device 50) is fixedly connected to the carrier element 43 that incorporates the magnet elements, whereas a housing of the potentiometer is attached to the housing 20 of the medical appliance 1. To achieve an adjustment of the controllable and/or regulatable device 50, its housing is therefore fixed on or in the medical appliance 1 in such a way as to enable cooperation with the setting element 44. The setting element 44 can thus be moved relative to the controllable and/or regulatable device 50. The housing of a rotary potentiometer, for example, is fixed in a position opposite to the carrier element 43 in the direction of the axis of rotation 100' at the end directed towards the interior of the appliance 1. The controllable and/or regulatable device 50 can also be designed, for example, as a valve or similar setting element. By way of the potentiometer, for example, adjustment to a particular resistance value can be accomplished.

Regarding the arrangement of the magnet elements 71, 81, care should be taken to orient them so as to produce mutual entrainment. This is ensured only when the magnetic field built up between the magnet elements of the two setting devices 30, 40 is altered when one of the setting devices moves, in such a way that the magnetic flux between the magnet elements is weakened. Now, in order to return the magnetic flux to its maximal value, the other setting device follows the first setting device, so that this movement can be used to produce the desired actuation of the setting element.

Therefore when a rotational movement of the setting devices is to be performed, care should be taken that the magnet elements 71, 81 are arranged so that no rotationally symmetric field is formed about the axes of rotation 100, 100' of the setting devices 30, 40, because if that were the case there would be no alteration of the magnetic flux during the rotational movement, with the result that no moment of torque would be transmitted.

In this exemplary embodiment, then, the rotational movement of the first setting device 30 is transferred to the second setting device 40 by way of the magnetic coupling. Then by way of the second setting device 40, which includes the shaft of the potentiometer, the desired resistance value is set. To accomplish this, the carrier element 43 must not make contact with the wall of the housing 20. Carrier element 43 and setting element are already kept in position by the typical configuration of the potentiometer.

In this embodiment magnet elements are provided at end faces of the setting devices 30, 40, at their ends 31, 42. Thus, for example, three permanent magnets 71, 71' (a third magnet element at the first setting device is not shown), constructed e.g. as bar magnets, are disposed at uniform distances from one another at the end face of the first setting device 30. The same applies to the end face of the second setting device 40. FIG. 1b shows the second setting device 40 in front view. The magnets 71, 71', 81, 81', 81" should be fixed to the setting devices 30, 40 in such a way, with respect to their polarity, as to enable magnetic coupling.

The magnet elements can be provided as permanent magnets and, where appropriate, also as ferromagnetic elements. In general at least one setting device includes at least one permanent magnet, which then cooperates with another permanent magnet and/or a ferromagnetic element at the opposite setting device, and in some cases also on the receiving element, to produce the magnetic coupling.

Alternatively, it would be possible to provide only ferromagnetic elements at one setting device, so that these together with the magnets on the opposite setting device bring about the magnetic coupling. Depending on the strength of the magnets employed, only one magnet can also be provided, or another arbitrary number of magnets. FIG. 4 (fourth embodiment) shows in a simplified representation (only parts of the setting devices 30, 40 are shown) the arrangement of only one magnet on each of the setting devices 30, 40. The first setting device 30 here includes a ferromagnetic element 72, while there is a bar magnet 81 on the second setting device 40. When two permanent magnets are mounted, attention must be paid to their polarity.

It should be pointed out that the gaps shown in the figures between the receiving element 60 and the setting device 30 are as a rule not present during practical application. They are merely used in the drawings so that the individual components can be clearly distinguished. The setting device 30 during practical application is preferably fixed to the receiving element 60 in such a way as to enable a sliding movement between these components that is substantially without play.

FIG. 2a shows part of the medical appliance 1 with a second preferred embodiment of the adjustment apparatus 10, again shown in a schematic side view, while FIG. 2b represents a front view of the first setting device 30 in this second preferred embodiment of the adjustment apparatus 10. The structure of the adjustment apparatus 10 corresponds substantially to that shown in FIG. 1a, except that here the magnetic coupling is produced by a different arrangement of magnet elements.

The first setting device 30 here is constructed with a horseshoe magnet 71, as can be seen in particular in FIG. 2a. The second setting device 40 is also constructed with a horseshoe magnet 81. The horseshoe magnets 71, 81 accomplish the function of the adjustment apparatus 10 in accordance with preferred embodiments of the invention in an especially simple and reliable manner. In this arrangement, in an upper region of the adjustment apparatus 10 the north pole N and south pole S at the setting devices 30 and 40 are opposite one another, whereas in a lower region the relative positions of south pole S and north pole N are reversed. A rotational movement of the first setting device 30 thus reliably entrains the second setting device 40. The magnets 71, 81 are here disposed in the setting devices 30, 40 in such a way that they are flush with the surrounding material, for instance plastic, at the end faces of the setting devices 30, 40. Hence the oppositely situated magnet elements 71, 81 are disposed as close to one another as possible, to produce a strong magnetic field.

FIG. 3 shows a part of the medical appliance 1 in which a third preferred embodiment of the adjustment apparatus 10 can be seen in schematic side view. This, too, functions in substantially the same way as that in FIG. 1a. In this case the first setting device 30 is constructed with two bar magnets 71, 71', which cooperate with another bar magnet 91 provided as a receiving element for the first setting device 30. The second setting device 40 includes as carrier element 43 two ferromagnetic elements 82, 82', so that the magnetic coupling is produced by the bar magnets 71, 71' of the first setting device 30 in combination with the ferromagnetic elements 82, 82' of the second setting device 40. The first setting device 30, constructed as a turning knob, is simultaneously retained particularly strongly on the receiving element owing to the interaction of the three bar magnets 71, 71', 91. The disposition of only one bar magnet at the first setting device would in principle suffice to produce the magnetic coupling and to retain the setting device 30. The figure is drawn schematically. For selection and arrangement of the magnet elements, care should be taken that any weakening of the magnetic field that might be caused by an interaction between the magnet elements of the first setting device and the magnet elements of the receiving element is inconsequential, or does not occur at all.

Figure 5:
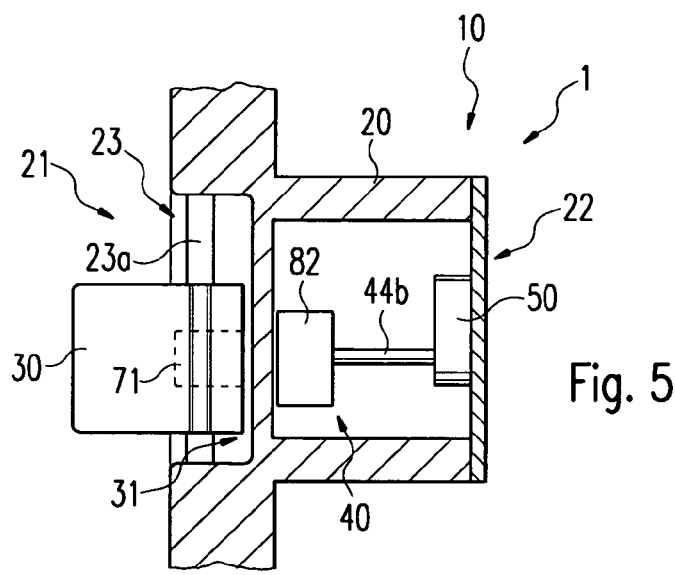
FIG. 5 illustrates part of a medical appliance with an adjustment apparatus in a fifth preferred embodiment, drawn schematically in side view.

FIG. 5 shows part of the medical appliance 1 in which a fifth preferred embodiment of the adjustment apparatus 10 can be seen in schematic side view. In contrast to the embodiments presented so far, the setting element is moved linearly; here it is shown as the setting element of a slide potentiometer. That is, a rod 44b (setting element of the slide potentiometer) attached to the second setting device 40 actuates the slide potentiometer that is fixed to the housing of the medical appliance 1, in order to change the resistance. The first setting device 30 is constructed so that it can be substantially linearly moved within a guide groove 23a of a guide means 23 on the outside 21 of the housing 20, and thereby causes the second setting device 40 to move correspondingly. To produce the magnetic coupling the first setting device 30 includes a bar magnet 71 disposed centrally in the setting device 30, in such a way as to be flush with the surface of the end that faces the housing. The second setting device includes a ferromagnetic element 82; that is, in this case it is the second setting device 40 that is constructed as a ferromagnetic element.

Actuation of the adjustment apparatus 10 by means of a first setting device 30 constructed as a sliding controller makes it possible for a reliable magnetic coupling to be maintained during the movements of the setting devices 30, 40.

Figure 6:
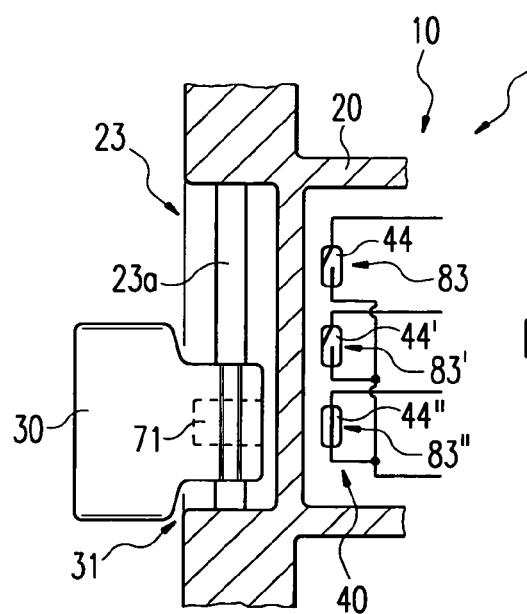
FIG. 6 illustrates part of a medical appliance with an adjustment apparatus in a sixth preferred embodiment, drawn schematically in side view.

In FIG. 6, a part of a medical appliance is shown in which a sixth preferred embodiment of the adjustment apparatus is represented in side view. The first setting device 30 here is similar to that shown in FIG. 5, so that the setting device 30 can be moved linearly on the housing of the medical appliance 1. In this exemplary embodiment, the second setting device 40 includes three reed contacts 83, 83', 83" as setting elements, which can be actuated in succession by shifting the first setting device 30. Thus the reed contacts can be used, e.g., to connect resistances of the controllable and/or regulatable device (not shown) so that a resistance change can be produced by shifting the first setting device 30. Here it is fundamentally possible to provide an arbitrary number of reed contacts. FIG. 6 shows the first setting device 30 positioned at a lower end of the guide means 23, where only the switch 83" is actuated. Movement of the setting device 30 towards an upper end of the guide means 23 would cause the switch 83' to be closed, while switch 83" is opened again because the magnet element 71 of the first setting device has been moved away from it. In this embodiment, therefore, the switch that is closed (so that, e.g., an associated resistance is connected) is always the one directly opposite the setting device 30 with a magnet 71 disposed thereon. Thus the switches are used, e.g., to connect resistances having various resistance values. The switching arrangement can also be constructed so that once a resistance has been connected, it remains in this state during actuation. For this purpose the actuating magnet element, for example, and the associated pathway should be appropriately designed.

The magnet elements of the first setting device 30 can thus alternatively be so designed and/or arranged that several switches can be actuated simultaneously.

It should be noted that all combinations of permanent magnets and ferromagnetic elements are possible, as long as they make it possible for the apparatus in accordance with preferred embodiments of the invention to function by way of magnetic coupling. Thus horseshoe magnets, annular magnets and bar magnets can cooperate with one another or else be combined with ferromagnetic elements. Furthermore, the magnet elements can be merely placed on the receiving element or also embedded therein.

At this juncture it should be pointed out that all of the parts described above are claimed as essential to the invention, individually or in any combination, in particular the details represented in the drawings. Modifications thereof are familiar to a person skilled in the art.

The invention claimed is:

1. A medical appliance with an adjustment apparatus, comprising:
   a first setting device disposed at an outer side of a housing the appliance; and
   a second setting device disposed in an interior of the appliance, the second setting device being designed to actuate a setting element for adjustment of a controllable and/or regulatable device,
   wherein the first setting device and the second setting device each comprises magnet elements, by which the first setting device cooperates with the second setting device in such a way that one of the first and second setting devices actuates the other of the first and second setting devices in order to mediate an adjustment of the controllable and/or regulatable device, such that the cooperation of the first and second setting devices is achieved by way of a magnetic coupling,
   wherein the first setting device is constructed such that the first setting device is placed on a receiving element, wherein the receiving element is formed so as to be integral with and protruding from the housing, such that the first setting device is then rotatably disposed on and surrounding the receiving element, wherein in order to transmit an adjustment in the form of a moment of torque by way of the setting devices, the magnet elements of the first setting device and the second setting device are disposed with respect to one another in such a way that they produce a magnetic field that is not rotationally symmetric with reference to an axis of rotation of the setting devices, so that during rotation of one of the setting devices the magnetic field between the magnet elements undergoes an alteration which produces mutual entrainment of the setting devices.

2. The medical appliance according to claim 1, wherein the magnet elements are constructed as permanent-magnet elements or ferromagnetic elements, such that at least one of the setting devices comprises at least one permanent-magnet element.

3. The medical appliance according to claim 1, wherein the first setting device and the second setting device are separated from one another by the housing, and are situated opposite one another, wherein the housing is constructed with no openings in a region within which the setting devices operate.

4. The medical appliance according to claim 1, wherein the actuation of the other of the first and second setting devices by the one of the first and second setting devices is achieved in that the one of the first and second setting devices entrains the other of the first and second setting devices.

5. The medical appliance according to claim 1, wherein the first setting device is designed to be disposed in a guide means on the housing, for holding and guiding the first setting device in such a way that it is shifted substantially linearly relative to the housing.

6. The medical appliance according to claim 1, wherein the first setting device is constructed as a knob element to be actuated by a user.

7. The medical appliance according to claim 1, wherein the second setting device comprises a carrier element on which at least one magnet element is disposed at an end directed towards the outside of the appliance, and on which the setting element for adjusting the controllable and/or regulatable device is attached at an end that is directed towards the interior of the appliance.

8. The medical appliance according to claim 1, wherein the controllable and/or regulatable device is constructed as one of a potentiometer, a valve or other similar device.

9. The medical appliance according to claim 1, wherein the setting element is constructed as one of a shaft for transferring a rotational movement and a rod for transferring a linear movement.

10. The medical appliance according to claim 1, wherein the first setting device comprises at least one magnet element disposed at an end face at an end of the first setting device directed towards the interior of the appliance, to produce a magnetic field during the magnetic coupling.

11. The medical appliance according to claim 1, wherein the second setting device comprises at least one magnet element disposed at an end face at an end of the second setting device directed towards the outside of the appliance, to produce a magnetic field during the magnetic coupling.

12. The medical appliance according to claim 1, wherein at least one of the first setting device and the second setting device comprises at least one of a horseshoe magnet and a bar magnet.

13. The medical appliance according to claim 1, wherein the first setting device is constructed so that it is fixed in position on the appliance by a force that is generated by the magnetic coupling.

14. The medical appliance according to claim 1, wherein the receiving element comprises at least one of permanent-magnet elements and ferromagnetic elements that cooperate with the magnet elements of at least one of an associated first setting device and an associated second setting device in such a way that the force generated by the magnetic coupling to hold at least the first setting device to the appliance is intensified.

15. The medical appliance according to claim 1, wherein the first setting device and the receiving element are so constructed that when the first setting device is placed on the receiving element it comes into locking engagement therewith.

16. The medical appliance according to claim 1, wherein the setting element is constructed as at least one reed contact for actuation and/or adjustment of the controllable and/or regulatable device, the first setting device being constructed so that during its actuation, the reed contact is actuated.

* * * * *